United States Patent
Melinte et al.

(10) Patent No.: US 6,699,509 B1
(45) Date of Patent: Mar. 2, 2004

(54) TATTOO REMOVAL

(76) Inventors: Silvia Melinte, 16659 E. Alwood St., Valinda, CA (US) 91744; Gavril S. Melinte, 16659 E. Alwood St., Valinda, CA (US) 91744

(*) Notice: Subject to any disclaimer, the term of this patent is extended or adjusted under 35 U.S.C. 154(b) by 0 days.

(21) Appl. No.: 09/953,604

(22) Filed: Sep. 17, 2001

(51) Int. Cl.[7] ............................................... A01N 59/16
(52) U.S. Cl. ..................... 424/618; 424/600; 424/641; 424/718
(58) Field of Search ............................... 424/600, 617, 424/618, 619, 641, 642, 400, 78.02, 718

(56) References Cited

PUBLICATIONS

Penoff, The Office Treatment of Tattoos a Simple and Effective Method, Plastic Reconstructive Surgery, (1987) 79 (2), 189–191.*

* cited by examiner

Primary Examiner—Jose G. Dees
Assistant Examiner—Sharmila S Gollamudi
(74) Attorney, Agent, or Firm—William W. Haefliger

(57) ABSTRACT

Three solution application method for tattoo removal.

11 Claims, No Drawings

TATTOO REMOVAL

BACKGROUND OF THE INVENTION

This invention relates generally to removal of tattoos from skin or skin areas; more specifically it concerns an effective and easily employed method to remove tattoos without scarring of the skin, and with minimum pain.

Considering the extent of tattoo application to many many people, and the desire of many such people to remove their tattoos' after periods of time, there is great need for an improved process of tattoo removal, without causing scarring of the skin, or undue damage to skin and flesh in tattoo areas.

SUMMARY OF THE INVENTION

It is a major object of the invention to provide a process or method for tattoo removal that will meet the need referred to.

Basically, the process of the invention is a three step process, such steps including:

- a) providing and applying to the skin area a first relatively strong acid solution that promotes mild blistering and raising of the outer skin layer,
- b) providing an applying to said raised skin area a second relatively weak acid solution characterized as gaining access to tattoo ink in the skin under said outer layer, and as dissolving said ink,
- c) removing said outer skin layer by scrubbing action,
- d) and providing and applying to the remaining skin area a third solution characterized as dissipating tattoo ink and as aiding in healing of skin to which the second solution was applied.

The process may also, and typically, include the step of protecting and allowing healing of the skin area to which said third solution has been applied. Such protecting may include bandaging of said skin area to which said third solution has been applied. Such bandaging is typically removed after at least two days, and then aqueously washing the skin area to which said third solution has been applied. An antibiotic substance may then be applied to the washed skin area.

Another object is to apply the three solutions to the skin area by swabbing, at intervals.

More specifically, the preferred method of the invention includes the steps:

- a) topically applying to the skin area a first solution consisting essentially of:
  - i) zinc acetate crystal
  - ii) benzene
  - iii) nitric acid, and
  - iv) distilled water, said application continuing at intervals until the top layer of the skin is raised,
- b) thereafter applying to the skin area a second solution that dissolves tattoo ink, said second solution consisting essentially of:
  - v) picric acid crystal
  - vi) propyl alcohol
  - vii) fragrance (optional)
  - viii) carbolic acid crystal
  - ix) acetic acid said second solution application continuing at intervals,
- c) gently removing the raised skin layer,
- d) and thereafter applying to the skin from which said raised layer has been removed, a third solution that consists essentially of
  - x) silver nitrate crystal
  - xi) methal alcohol and
  - xii) distilled water said third solution application continuing at intervals,
- e) bandaging the treated skin area, and after at least two days removing the bandaging, and washing the treated skin area.

In such method, weight parts may be substituted for gram weighting of constituents.

In the above the first referenced intervals are about 2 to 3 minute duration intervals, and which are repeated about 5 or 6 times; the second referenced intervals are about 2–3 minute duration intervals, and which are repeated about 5 or 6 times; and applications of the third solution is repeated 3 or 4 times. Such intervals are typically increased, for deeper and stronger tattoos.

More specifically, the three solution application steps include the following:

- a) typically applying to the skin area a first solution consisting proportionally of
  - i) about 0.5 grams of zinc acetate crystal
  - ii) about 0.5 grams of benzene,
  - iii) about 20 grams of nitric acid 90%
  - iv) about 19 grams of distilled water, said application being repeated at first intervals until the top layer of the skin becomes raised,
- b) thereafter applying to the skin area a second solution that dissolves tattoo ink, said second solution consisting proportionally of
  - v) about 0.5 grams of picric acid crystal
  - vi) about 1.0 grams of propyl alcohol
  - vii) optionally about 0.05 grams of fragrance
  - viii) about 1.0 grams of carabolic acid crystal,
  - ix) about 97.45 grams of acetic acid 98%, said second solution application being repeated at second intervals to effect dissolving of tattoo ink,
- c) gently scrubbing and removing the raised skin layer,
- d) and thereafter applying to the skin area from which raised skin layer has been removed, a third solution consisting proportionally of:
  - iv) about 15.0 grams of silver nitrate crystal
  - v) about 2.0 grams of methyl alcohol
  - vi) about 83.0 grams of distilled water said application being repeated at intervals,
- e) and thereafter protecting and allowing healing of the skin area to which said third solution has been applied.

In the stated method or methods, step 2, the "fragrance" may consist of Lavender. The crystal forms of certain constituents may consist of tiny crystal grains which are soluble.

Even more specifically, the preferred procedure consists of employing three different chemical mixtures applied directly onto the tattooed skin.

Solution #1 when applied prepares the skin to become receptive to solution #2.

| Composition of solution #1: | |
|---|---|
| Zinc acetate crystal | 0.5 grams |
| Benzene | 0.5 grams |
| Nitric Acid 90% | 20 grams |
| Distilled water | 29 grams |

Application: Apply solution #1 with a cotton swab 5–6 times at approximately 2–3 minute intervals until the top layer of the skin is raised.

Solution #2 breaks down the tattoo inks; and attacks and dissolves the ink.

| Composition of solution #2: | |
| --- | --- |
| Picric Acid crystal | 0.5 grams |
| Propyl Alcohol | 1.0 grams |
| Fragrance | 0.05 grams |
| Carbolic Acid crystal | 1.0 grams |
| Acetic Acid 98% | 97.45 grams |

Application: Apply solution #2 with a cotton swab 5–6 times at approximately 2–3 minute intervals. With a sterile tongue depressor (wooden), scrub the treated area to gently remove the raised skin layer(s). After removing the skin, apply solution #3.

Solution #3 will complete the dissipation of the tattoo inks and aids in the healing process of the skin by neutralizing the action of solution #2.

| Composition of solution #3: | |
| --- | --- |
| Silver Nitrate crystal | 15.05 grams |
| Methyl Alcohol | 2.0 grams |
| Distilled water | 83.0 grams |

Application: Apply solution #3 3–4 times with a cotton swab.

Apply sterile gauze onto the treated area and tape with medical tape to stay in place.

Leave the bandage in place for 5–6 days. Do not make contact with water.

Remove the bandage. Wash the treated area with soap and water. Apply an over the counter antibiotic ointment to aid in the healing process. One such ointment is Neosporin, Triple-Antibiotic Oint.

Zones of the skin, about 4 square inch in area, may be individually treated, as in succession. The process can be carried out at ambient temperature or temperatures.

We claim:

1. The method of removing an undesirable tattoo from a skin area, that includes the steps:
    a) topically applying to the skin area a solution consisting essentially of:
        i) zinc acetate crystal
        ii) benzene
        iii) nitric acid, and
        iv) distilled water,
    said application continuing at intervals until the top layer of the skin is raised,
    b) thereafter applying to the skin area a second Solution that dissolves tattoo ink, said second solution consisting essentially of:
        v) picric acid crystal
        vi) propyl alcohol
        vii) fragrance
        viii) carbolic acid crystal
        ix) acetic acid
    said second solution application continuing at intervals,
    c) gently removing the raised skin layer,
    d) and thereafter applying to the skin from which said raised layer has been removed, a third solution that consists essentially of
        x) silver nitrate crystal,
        xi) methyl alcohol and
        xii) distilled water,
    said third solution application continuing at intervals,
    e) bandaging the treated skin area, and after at least two days removing the bandaging and washing the treated skin area.

2. The method of claim 1 in including subsequently applying an antibiotic ointment to the washed skin area.

3. The method of claim 1 wherein said first, second and third solution applications being effected by swabbing of solution onto the skin area.

4. The method of removing an undesirable tattoo from a skin area, that includes the steps;
    a) topically applying to the skin area a first solution consisting proportionally of
        i) about 0.5 grams of zinc acetate crystal
        ii) about 0.5 grams of benzene,
        iii) about 20 grams of nitric acid 90%
        iv) about 19 grams of distilled water,
    said application being repeated at first intervals until the top layer of the skin becomes raised,
    b) thereafter applying to the skin area a second solution that dissolves tattoo ink, said second solution consisting proportionally of
        v) about 0.5 grams of picric acid crystal
        vi) about 1.0 grams of propyl alcohol
        vii) optionally about 0.05 grams of fragrance
        viii) about 1.0 grams of carbolic acid crystal
        ix) about 97.45 grams of acetic acid 98%,
    said second solution application being repeated at second intervals to effect dissolving of tattoo ink,
    c) gently scrubbing and removing the raised skin layer, and
    d) and thereafter applying to the skin area from which raised skin layer has been removed, a third solution consisting proportionally of:
        x) about 15.0 grams of silver nitrate crystal
        xi) about 2.0 grams of methyl alcohol
        xii) about 83.0 grams of distilled water
    said application being repeated at intervals,
    e) and thereafter protecting and allowing healing of the skin area to which said third solution has been applied.

5. The method of claim 4 wherein said protecting includes bandaging of said skin area to which said third solution has been applied.

6. The method of claim 5 which includes removing said bandaging after at least two days, and aqueously washing the skin area to which said third solution has been applied.

7. The method of claim 6 which includes subsequently applying an antibiotic substance to the washed skin area.

8. The method of claim 4 wherein said first, second and third solution applications are effected by swabbing of solution onto the skin area.

9. The method of claim 4 wherein said first intervals are about 2 to 3 minute duration intervals, and which are repeated about 5 or 6 times.

10. The method of claim 4 wherein said second intervals are about 2–3 minute duration intervals, and which are repeated about 5 or 6 times.

11. The method of claim 4 wherein said application of third solution is repeated 3 or 4 times.

* * * * *